(12) United States Patent
Andersson et al.

(10) Patent No.: US 7,261,859 B2
(45) Date of Patent: Aug. 28, 2007

(54) MICROANALYSIS DEVICE

(75) Inventors: Per Andersson, Stockholm (SE); Arvi Aksberg, Lidingö (SE); Gunnar Ekstrand, Uppsala (SE); Björn Berg, Uppsala (SE)

(73) Assignee: Gyros AB, Uppsala (SE)

( * ) Notice: Subject to any disclaimer, the term of this patent is extended or adjusted under 35 U.S.C. 154(b) by 544 days.

(21) Appl. No.: 10/169,056

(22) PCT Filed: Dec. 22, 2000

(86) PCT No.: PCT/EP00/13145

§ 371 (c)(1),
(2), (4) Date: Sep. 25, 2002

(87) PCT Pub. No.: WO01/46465

PCT Pub. Date: Jun. 28, 2001

(65) Prior Publication Data
US 2003/0143114 A1  Jul. 31, 2003

(30) Foreign Application Priority Data
Dec. 23, 1999 (WO) .................. PCT/EP99/10347
May 12, 2000 (SE) ........................... 0001779

(51) Int. Cl.
*G01N 21/07* (2006.01)

(52) U.S. Cl. .............. 422/72; 422/100; 422/101; 422/102; 436/45; 436/180; 494/10

(58) Field of Classification Search .......... 436/45, 436/180; 422/72, 100, 102, 101; 137/246, 137/546, 571, 627, 583–589, 247.11, 247.13; 494/10, 11, 13
See application file for complete search history.

(56) References Cited

U.S. PATENT DOCUMENTS

| | | | |
|---|---|---|---|
| 3,547,547 A | | 12/1970 | Anderson |
| 4,284,602 A | | 8/1981 | Kelton et al. |
| 4,330,080 A | * | 5/1982 | Mathieu ............... 494/43 |
| 4,859,420 A | * | 8/1989 | Schultz ............... 422/58 |
| 5,160,702 A | | 11/1992 | Kopf-Sill et al. |
| 5,376,252 A | | 12/1994 | Ekstrom |
| 5,591,643 A | | 1/1997 | Schembri |

(Continued)

OTHER PUBLICATIONS

U.S. Appl. No. 09/674,457, filed Jan. 5, 2001, Larsson et al.

(Continued)

*Primary Examiner*—Jan M. Ludlow
(74) *Attorney, Agent, or Firm*—Fulbright & Jaworski LLP

(57) ABSTRACT

Microstructure for fluids provided in a rotatable disc (D) having a U-shaped volume-defining structure (7) connected at its base to an inlet arm of a U-shaped chamber (10).

20 Claims, 11 Drawing Sheets

U.S. PATENT DOCUMENTS

| | | | |
|---|---|---|---|
| 5,690,841 A | 11/1997 | Elderstig | |
| 5,693,233 A * | 12/1997 | Schembri | 210/787 |
| 5,773,488 A | 6/1998 | Allmer | |
| 5,919,711 A * | 7/1999 | Boyd et al. | 436/178 |
| 5,962,081 A | 10/1999 | Ohman | |
| 5,995,209 A | 11/1999 | Ohman | |
| 6,002,475 A * | 12/1999 | Boyd et al. | 356/246 |
| 6,033,914 A * | 3/2000 | Boyd et al. | 436/178 |
| 6,126,765 A | 10/2000 | Ohman | |
| 6,144,447 A | 11/2000 | Ohman | |
| 6,192,768 B1 | 2/2001 | Wallman | |
| 6,203,291 B1 | 3/2001 | Stemme | |
| 6,299,839 B1 * | 10/2001 | Karunaratne et al. | 422/63 |
| 6,322,682 B1 | 11/2001 | Arvidsson | |
| 6,454,970 B1 | 9/2002 | Ohman | |
| 6,499,499 B2 | 12/2002 | Dantsker et al. | |
| 6,620,478 B1 | 9/2003 | Ohman | |
| 6,632,656 B1 | 10/2003 | Thomas | |
| 6,653,625 B2 | 11/2003 | Andersson | |
| 6,717,136 B2 | 4/2004 | Andersson | |
| 6,728,644 B2 | 4/2004 | Bielik | |
| 6,811,736 B1 | 11/2004 | Ohman | |
| 6,812,456 B2 | 11/2004 | Andersson | |
| 6,812,457 B2 | 11/2004 | Andersson | |
| 6,852,851 B1 | 2/2005 | Tooke et al. | |
| 2002/0125135 A1 | 9/2002 | Derand et al. | |
| 2003/0029724 A1 | 2/2003 | Derand et al. | |
| 2003/0044322 A1 | 3/2003 | Andersson | |
| 2003/0047823 A1 | 3/2003 | Ohman | |
| 2003/0053934 A1 | 3/2003 | Andersson | |
| 2003/0054563 A1 | 3/2003 | Ljungstrom | |
| 2003/0064004 A1 | 4/2003 | Agren | |
| 2003/0082075 A1 | 5/2003 | Agren | |
| 2003/0094502 A1 | 5/2003 | Andersson | |
| 2003/0129360 A1 | 7/2003 | Derand | |
| 2003/0146155 A1 | 8/2003 | Tooke et al. | |
| 2003/0156763 A1 | 8/2003 | Soderman | |
| 2003/0173650 A1 | 9/2003 | Larsson et al. | |
| 2003/0211012 A1 | 11/2003 | Bergstrom | |
| 2003/0213551 A1 | 11/2003 | Derand | |
| 2003/0231312 A1 | 12/2003 | Sjoberg | |
| 2004/0005634 A1 | 1/2004 | Kylberg et al. | |
| 2004/0055136 A1 | 3/2004 | Ohman et al. | |
| 2004/0058408 A1 | 3/2004 | Thomas | |
| 2004/0096867 A1 | 5/2004 | Andersson | |
| 2004/0099310 A1 | 5/2004 | Andersson | |
| 2004/0120856 A1 | 6/2004 | Andersson | |
| 2004/0131345 A1 | 7/2004 | Kylberg et al. | |
| 2004/0202579 A1 | 10/2004 | Larsson et al. | |
| 2005/0019819 A1 | 1/2005 | Tooke et al. | |
| 2005/0042770 A1 | 2/2005 | Derand et al. | |
| 2005/0141344 A1 | 6/2005 | Ekstrand et al. | |
| 2005/0179901 A1 | 8/2005 | Ostlin et al. | |

OTHER PUBLICATIONS

U.S. Appl. No. 09/830,795, filed Oct. 29, 1999, Stjernstrom.
U.S. Appl. No. 09/869,554, filed Dec. 23, 1999, Orlefors et al.
U.S. Appl. No. 09/937,533, filed Nov. 27, 2001, Larsson et al.
U.S. Appl. No. 09/958,577, filed Apr. 7, 2000, Ulfendahl.
U.S. Appl. No. 10/030,297, filed Dec. 21, 2001, Derand et al.
U.S. Appl. No. 10/070,912, filed Mar. 13, 2002, Ohman et al.
U.S. Appl. No. 10/129,032, filed Apr. 30, 2002, Tormod.
U.S. Appl. No. 10/513,084, filed Oct. 26, 2004, Holmquest et al.
U.S. Appl. No. 10/867,893, filed Jun. 15, 2004, Derand et al.
U.S. Appl. No. 11/017,252, filed Dec. 20, 2004, Larsson et al.

* cited by examiner

MICROANALYSIS DEVICE

FIELD OF THE INVENTION

The present invention relates to microanalysis devices and methods for moving fluids in such devices.

PRIOR ART

The idea is applicable to (but not limited to) microanalysis systems that are based on microchannels formed in a rotatable, usually plastic, disc, often called a "centrifugal rotor" or "lab on a chip". Such discs can be used to perform analysis and separation on small quantities of fluids. In order to reduce costs it is desirable that the discs should be not restricted to use with just one type of reagent or fluid but should be able to work with a variety of fluids. Furthermore it is often desirable during the preparation of samples that the disc permits the user to dispense accurate volumes of any desired combination of fluids or samples without modifying the disc. Due to the small widths of the microchannels, any air bubbles present between two samples of fluids in the microchannels can act as separation barriers or can block the microchannel and thereby can prevent a fluid from entering a microchannel that it is supposed to enter. In order to overcome this problem U.S. Pat. No. 5,591,643 teaches the use of a centrifugal rotor which has microchannels that have cross sectional areas which are sufficiently large that unwanted air can be vented out of the microchannel at the same time as the fluid enters the microchannel.

OBJECT OF THE INVENTION

An object of the present invention is to provide a structure for a centrifugal rotor and a method for using such a centrifugal rotor, which structure and which method permits the reliable transport of fluids in the centrifugal rotor.

A further object of the present invention is to provide a structure for a centrifugal rotor and a method for using such a centrifugal rotor, which structure and which method permits the accurate metering of fluids in the centrifugal rotor.

SUMMARY OF THE INVENTION

The present invention achieves the objects of the invention by means of a structure having the features of claim 1. A method for using such a structure to achieve the objects of the invention has the features of claim 5.

BRIEF DESCRIPTION OF THE FIGURES

The present invention will be illustrated by a non-limiting example of an embodiment by means of the following figures, where.

DETAILED DESCRIPTION OF EMBODIMENTS ILLUSTRATING THE INVENTION

Figure 1A:
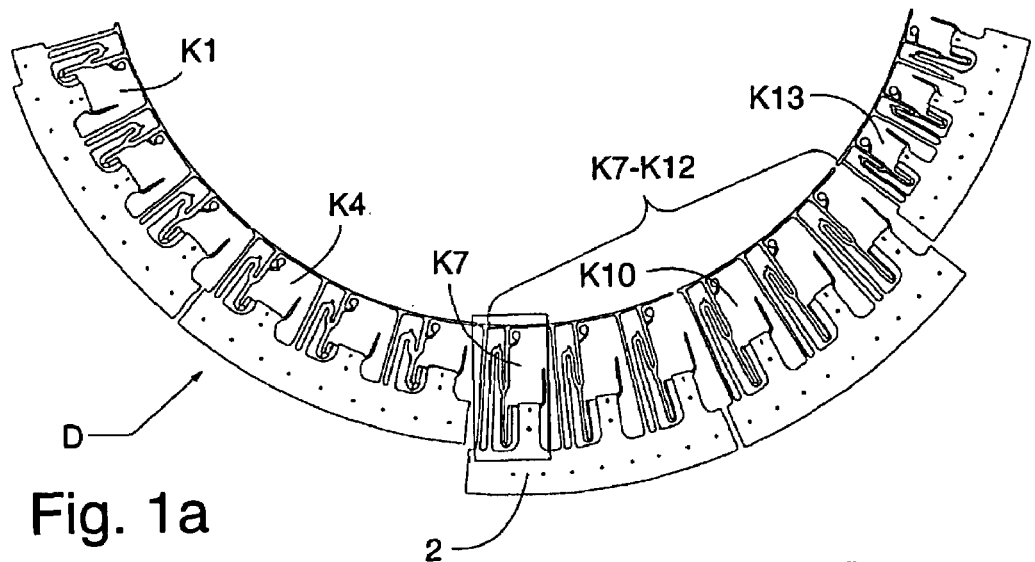
FIG. 1a shows the peripheral part of a centrifugal rotor having five radially extending microchannel structures K7-K12 in accordance with the present invention.

The microchannel structures (K7-K12) in accordance with the present invention are shown in FIGS. 1a-d arranged radially on a microfluidic disc (D). Suitably the microfluidic disc is of a one- or two-piece moulded construction and is formed of an optionally transparent plastic or polymeric material by means of separate mouldings which are assembled together (e.g. by heating) to provide a closed structure with openings at defined positions to allow loading of the device with fluids and removal of fluid samples. Suitable plastic of polymeric materials may be selected to have hydrophobic properties. Preferred plastics or polymeric materials are selected from polystyrene and polycarbonate. In the alternative, the surface of the microchannels may be additionally selectively modified by chemical or physical means to alter the surface properties so as to produce localised regions of hydrophobicity or hydrophilicity within the microchannels to confer a desired property. Preferred plastics are selected from polymers with a charged surface, suitably chemically or ion-plasma treated polystyrene, polycarbonate or other rigid transparent polymers.

The microchannels may be formed by micro-machining methods in which the micro-channels are micro-machined into the surface of the disc, and a cover plate, for example, a plastic film is adhered to the surface so as to enclose the channels. The microfluidic disc (D) has a thickness which is much less than its diameter and is intended to be rotated around a central hole so that centrifugal force causes fluid arranged in the microchannels in the disc to flow towards the outer periphery of the disc. In the embodiment of the present invention shown in FIG. 1a-1d, the microchannels start from a common, annular inner application channel (1) and end in common, annular outer waste channel (2), substantially concentric with channel (1). It is also possible to have individual application channels (waste channels for each microchannel or a group of microchannels. Each inlet opening (3) of the microchannel structures (K7-K12) may be used as an application area for reagents and samples. Each microchannel structure (K7-K12) is provided with a waste chamber (4) that opens into the outer waste channel (2). Each microchannel (K7-K12) forms a U-shaped volume-defining structure (7) and a U-shaped chamber (10) between its inlet opening (3) and the waste chamber (4). The normal desired flow direction is from the inlet opening (3) to the waste chamber (4) via the U-shaped volume-defining structure (7) and the U-shaped chamber (10). Flow can be driven by capillary action, pressure and centrifugal force, i.e. by spinning the disc. As explained later, hydrophobic breaks can also be used to control the flow. Radially extending waste channels (5), which directly connect the annular inner channel (1) with the annular outer waste channel (2), in order to remove an excess fluid added to the inner channel (1), are also shown.

Thus, fluid can flow from the inlet opening (3) via an entrance port (6) into a volume-defining structure (7) and from there into a first arm of a U-shaped chamber (10). The volume-defining structure (7) is connected to a waste outlet for removing excess fluid, for example, radially extending waste channel (8) which waste channel (8) is preferably connected to the annular outer waste channel (2). The waste channel (8) preferably has a vent (9) that opens into open air via the top surface of the disk. Vent (9) is situated at the part of the waste channel (8) that is closest to the centre of the disc and prevents fluid in the waste channel (8) from being sucked back into the volume-defining structure (7).

The chamber (10) has a first, inlet arm (10a) connected at its lower end to a base (10c) which is also connected to the lower end of a second, outlet arm (10b). The chamber (10) may have sections I, II, III, IV which have different depths, for example each section could be shallower than the preceding section in the direction towards the outlet end, or alternatively sections I and III could be shallower than sections II and IV, or vice versa. A restricted waste outlet (11), i.e. a narrow waste channel, is provided between the chamber (10) and the waste chamber (4). This makes the resistance to fluid flow through the chamber (10) greater than the resistance to fluid flow through the path that goes through volume-defining structure (7) and waste channel (8).

Due to the relatively large width of the waste chamber (4), the top and bottom surfaces of the waste chamber (4) are preferably separated by one or more supports (12) to ensure that the top and bottom surfaces of the microfluidic device do not bend inwards towards the waste chamber (4) and thereby change its volume.

Figure 1B:
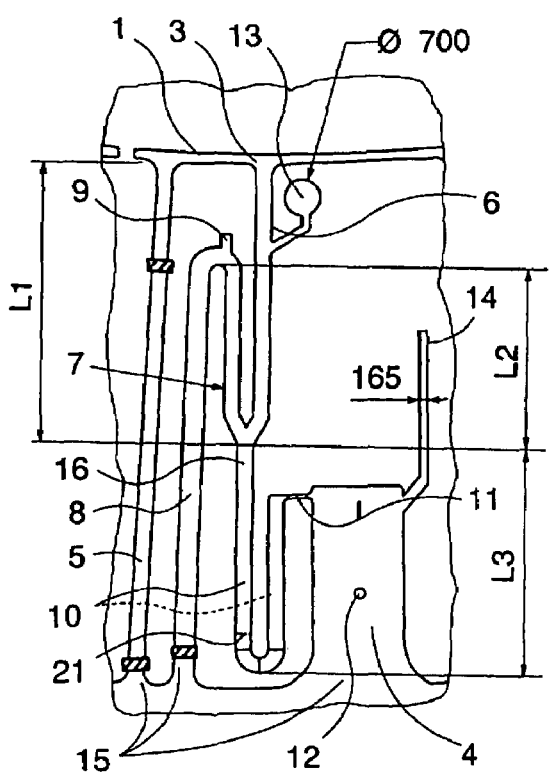
FIG. 1b shows an enlarged view of one microchannel structure from FIG. 1a in accordance with the present invention.
Figure 1C:
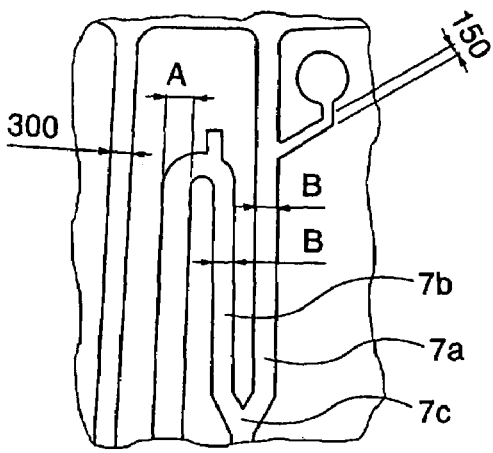
FIG. 1c shows an enlarged view of a sample volume-defining structure in the microchannel structure of FIG. 1b.
Figure 1D:
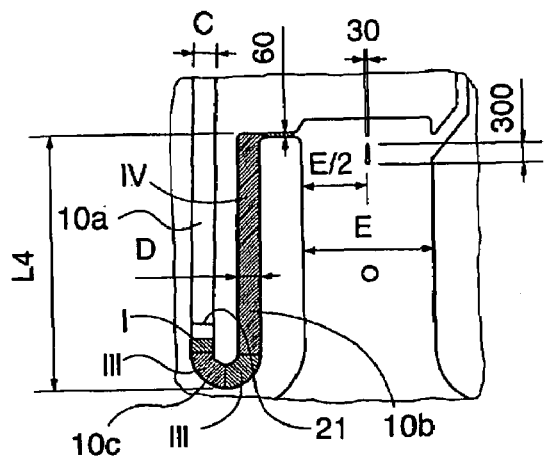
FIG. 1d shows an enlarged view of the chamber area plus chambers for the disposal of waste fluids, wherein variations in depth are shown by cross-hatching.

As shown in FIGS. 1a-c, the volume-defining structure (7) is U-shaped with the entrance port (6) opening into the upper end (i.e. the end nearest to the centre of the disc) of one of the arms (7a) of the U and the waste channel (8) connected to the upper end of the other arm (7b) of the U. The vent (9) is also placed at the top of this other arm (7b). The base (7c) of the U-formed volume-defining structure (7) is connected to the upper end of a first arm (10a) of the chamber (10).

In addition to the application area at the inlet (3) of the structure, there may also be an additional application area (13) that opens out into the top surface of the disc and is connected to the entrance port (6). This additional application area (13) can be used when it is desired to add different reagents or samples to each of the different microstructures (K7-K12).

There is preferably also a vent (14) to open air in the chamber (10). A hydrophobic break is preferably provided at the connection (16) of the chamber (10) to the volume-defining structure (7) in order to guide fluid into arm (7b)

The outer annular waste channel (2) may be sectioned so as to collect waste from a selected number of closely located microchannel structures.

Hydrophobic breaks can be introduced into the microchannel structures (K7-K12), for example by marking with an over-head pen (permanent ink) (Snowman pen, Japan), and suitable places for such breaks (shown by crosshatching in the figures) include: (a) between microchannel structure inlets (3) in the inner annular application channel (1), (b) each opening (15) into the outer annular waste channel (i.e. the openings of the waste chambers) and, (c) if present, also the radial waste channels (5) which connect the inner annular application channel (1) and the outer annular waste channel (2), and also the waste channel (8) which guides away excess fluid from the volume-defining structure (7).

The purpose of the hydrophobic breaks is to prevent capillary action from drawing the fluid into undesired directions. Hydrophobic breaks can be overcome by centrifugal force i.e. by spinning the disc at high speed.

If the sample to be analysed is in the form or cells or sedimenting material or particles then it can be held in the lower U-channel by a particle filter (21) (shown by a dotted line in FIG. 1b and 1d) or the flow through the chamber (10) can be controlled such that particles are retained in the chamber while fluids flow through it—as will be described later.

Figure 2A:
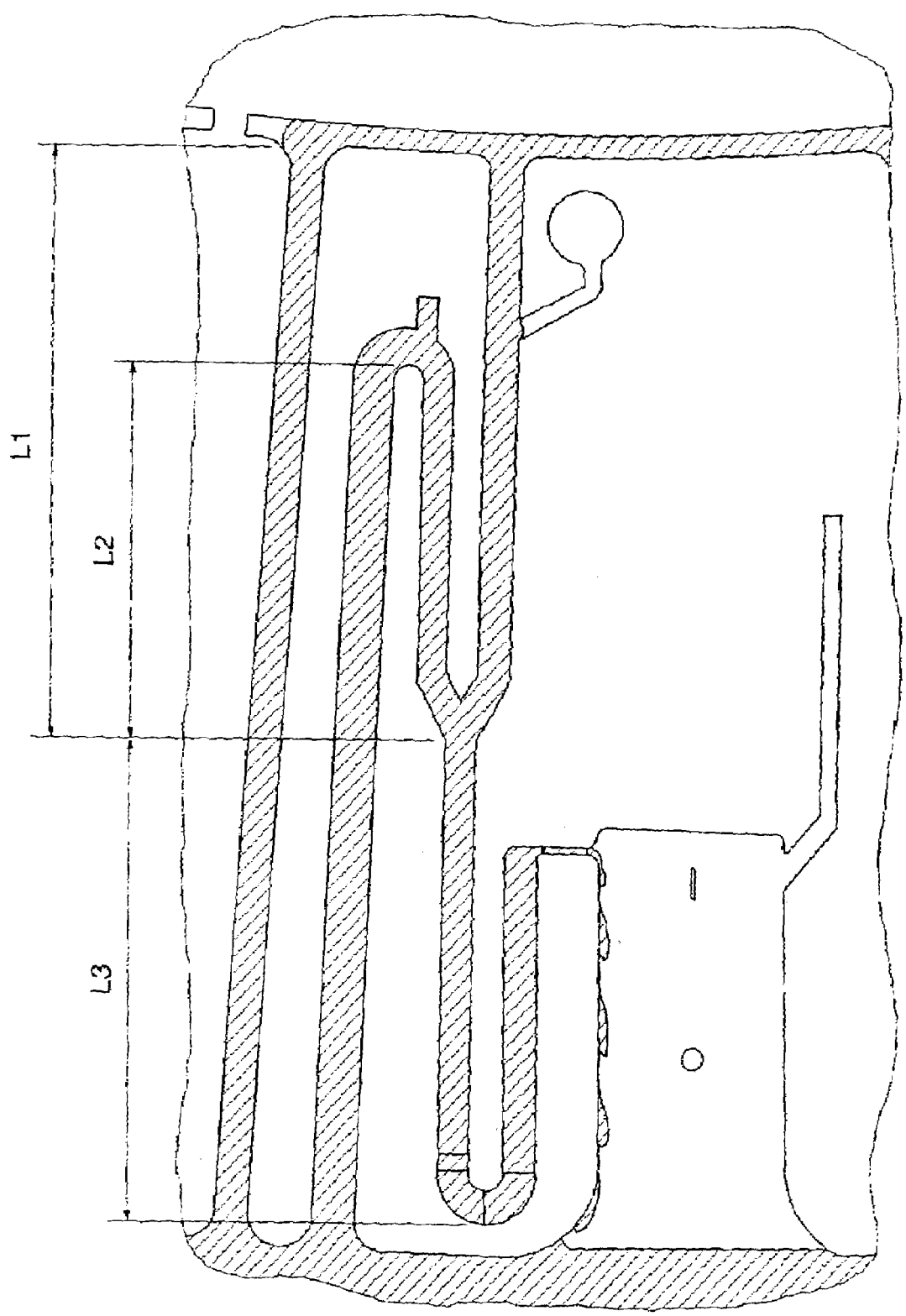
FIGS. 2a and 2b show the structure of FIG. 1b with the chamber containing a first fluid.
Figure 2B:
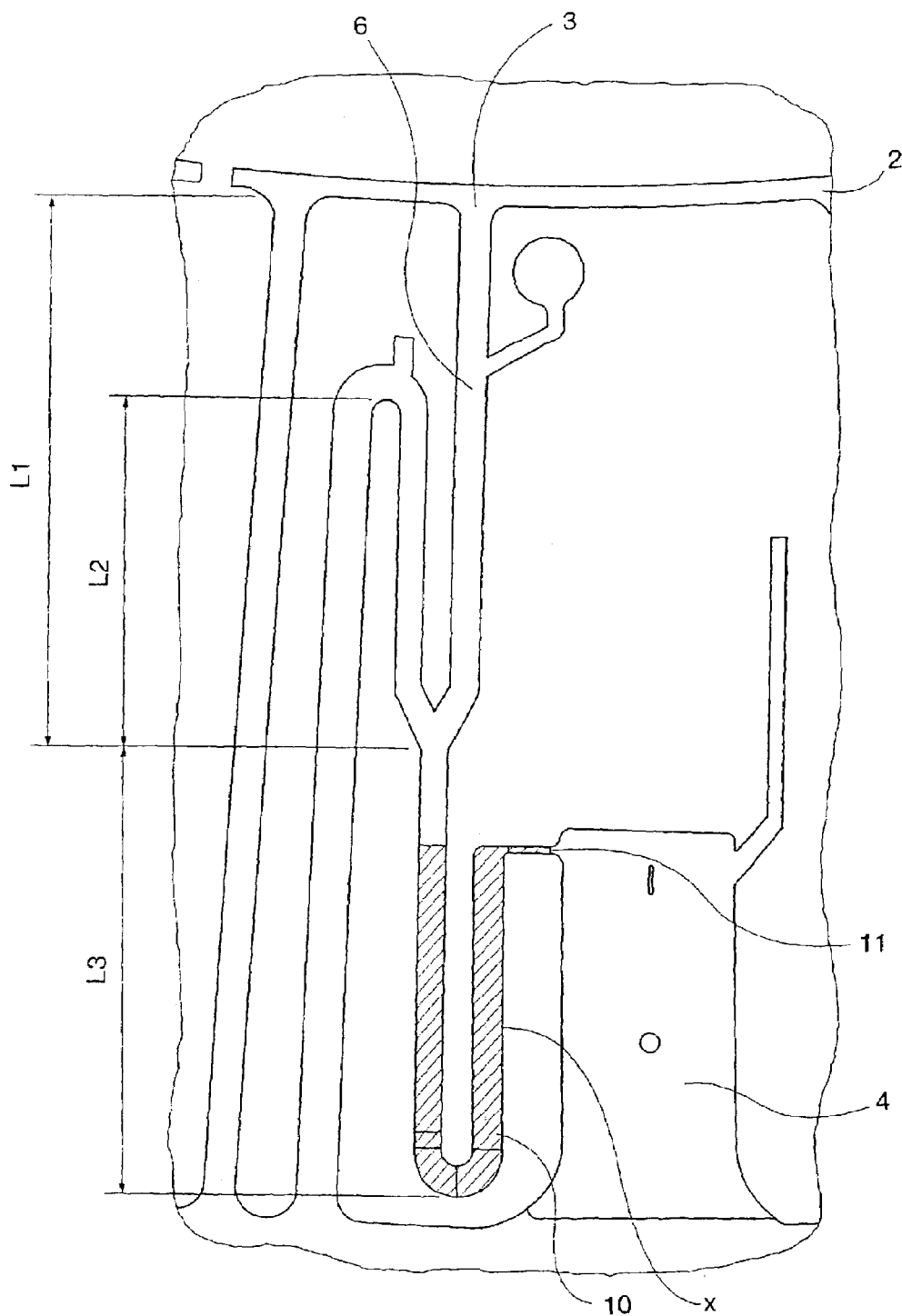

A first reagent or sample fluid X can be introduced into the chamber (10) by connecting a source (not shown) of the fluid X to the common annular inner application channel (1) from where it flows by capillary action and/or, if the disc is spun, centrifugal force to the lower U-bend. If the volume of fluid X which is introduced into common annular inner application channel (1) is in excess (i.e. is greater than the volume of the chamber (10) up to the level of the restricted channel (11) (distance L4 in FIG. 1d)) then some of it flows to waste via the radial waste channel (5) while the rest flows to waste chamber (4) via the chamber (10) though the restricted channel (11) as shown in FIG. 2. This continues until the levels of fluid X in both the left hand and right hand arms of the chamber (10) are the same as the distance L4, i.e. the U-shaped chamber is full up to the level of the restricted channel (11). This is shown in FIG. 2b) where the excess fluid X has flowed out of the microchannel structure via the waste chamber (4) and radial waste channel (5) to the outer waste channel (2) or via the restricted channel (11).

Figure 3A:
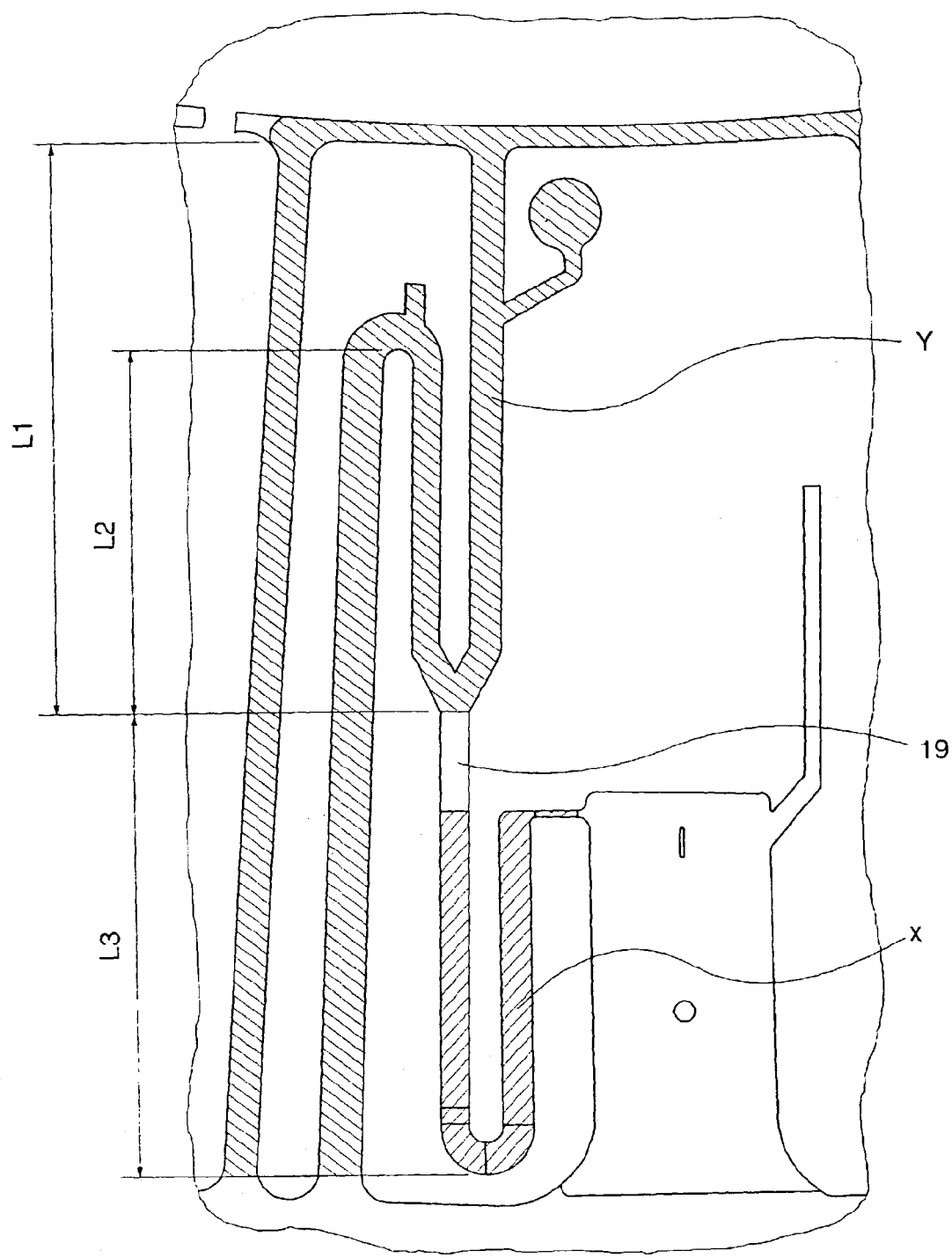
FIGS. 3a and 3b shows the addition of a second fluid to a volume-defining chamber.

When it is time to add a new reagent or sample fluid Y, then fluid Y is added by the common annular inner application channel (1) (or, alternatively, as shown in FIG. 3a) by the additional application area (13)). The fluid Y travels by capillary action through the volume-defining structure (7) and down the waste channel (5) as shown in FIG. 3a). It cannot flow into chamber (10) as the air cushion (19) contained between the base of the volume defining structure and the top of the fluid in arm (7a) of the chamber acts as a barrier to prevent the fluid flowing into chamber 10. Note that optionally an air cushion (19) can be left between the first fluid X and the second fluid Y by making the distance L4 from the base of the U-bend in the chamber (10) to the restricted channel (11) less than the distance L3 from the base of the U-bend in the chamber (10) to the base of the U-bend of the volume-defining structure (7).

Figure 3B:
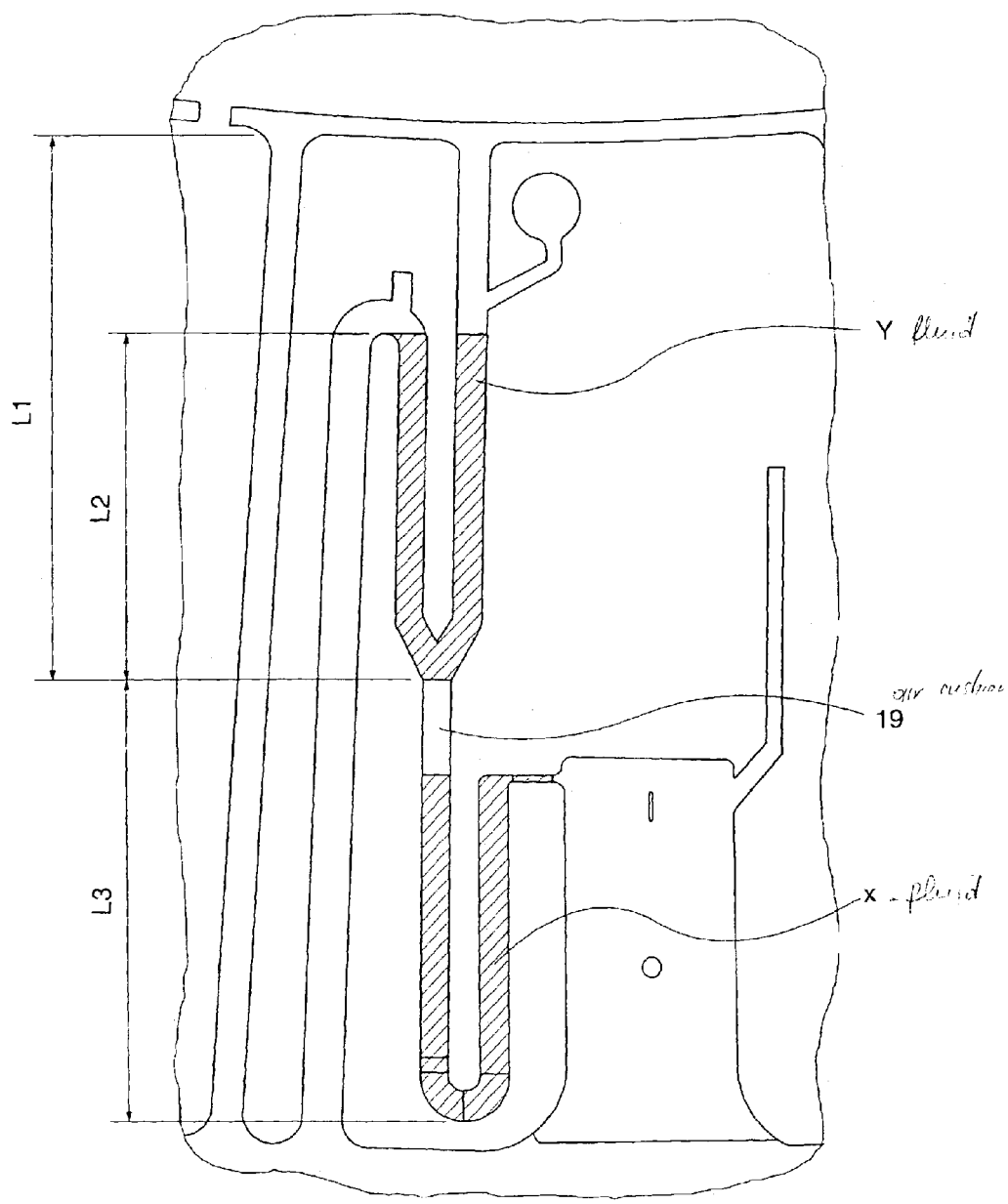

This can prevent the second fluid Y from flowing by capillary action into the chamber (10) and can also prevent mixing of the fluids X and Y. The vent (9), which is open to atmospheric pressure, makes it easier for the second fluid Y to flow towards the waste channel (5). Gentle, i.e. low speed, spinning of the disc (D) empties the excess fluid Y from waste channel (5), leaving the volume-defining structure (7) full of fluid Y, as shown in FIG. 3b).

Figure 4A:
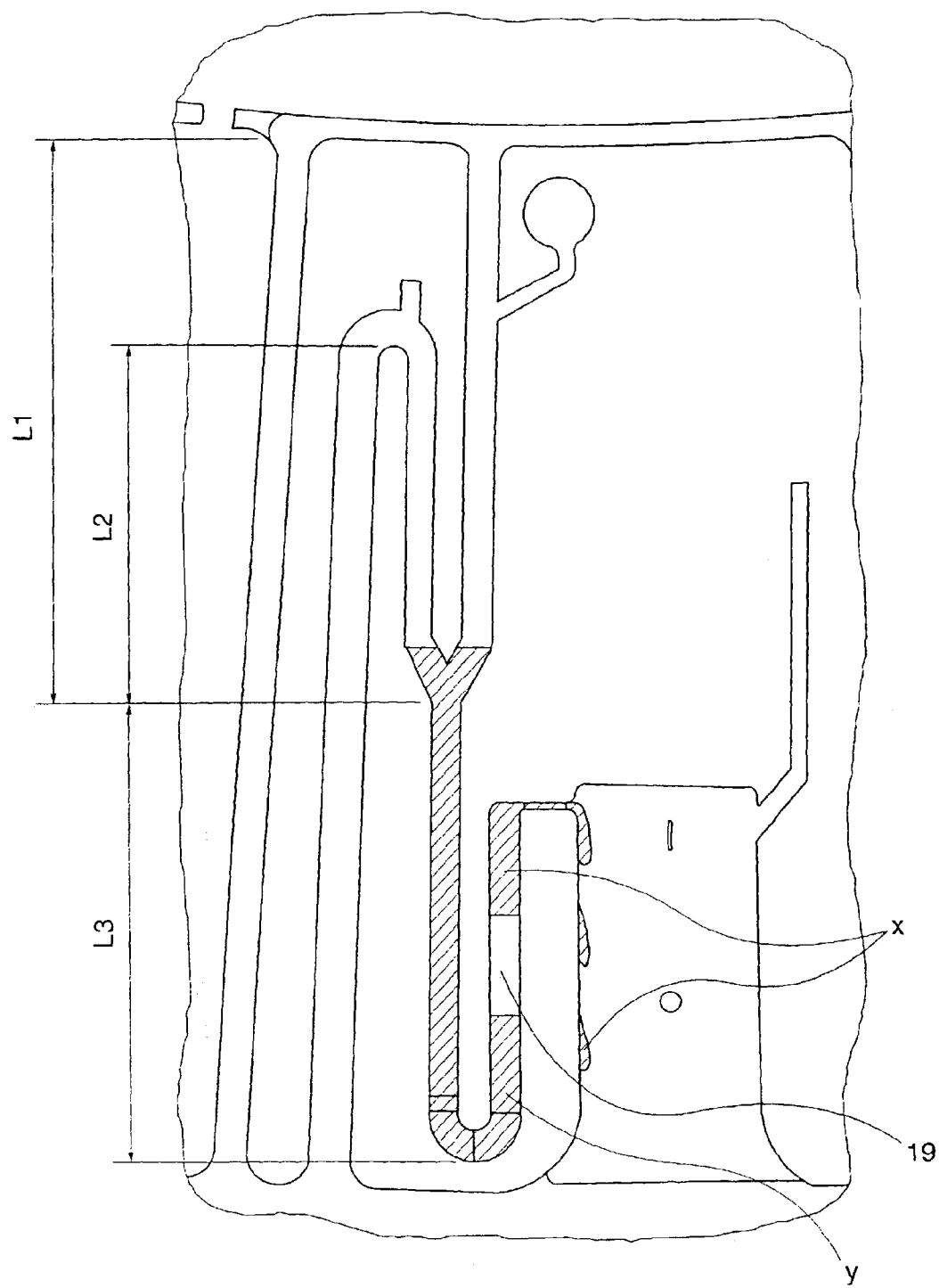
FIGS. 4a and 4b show the replacement of the first fluid in the chamber by said second fluid.
Figure 4B:
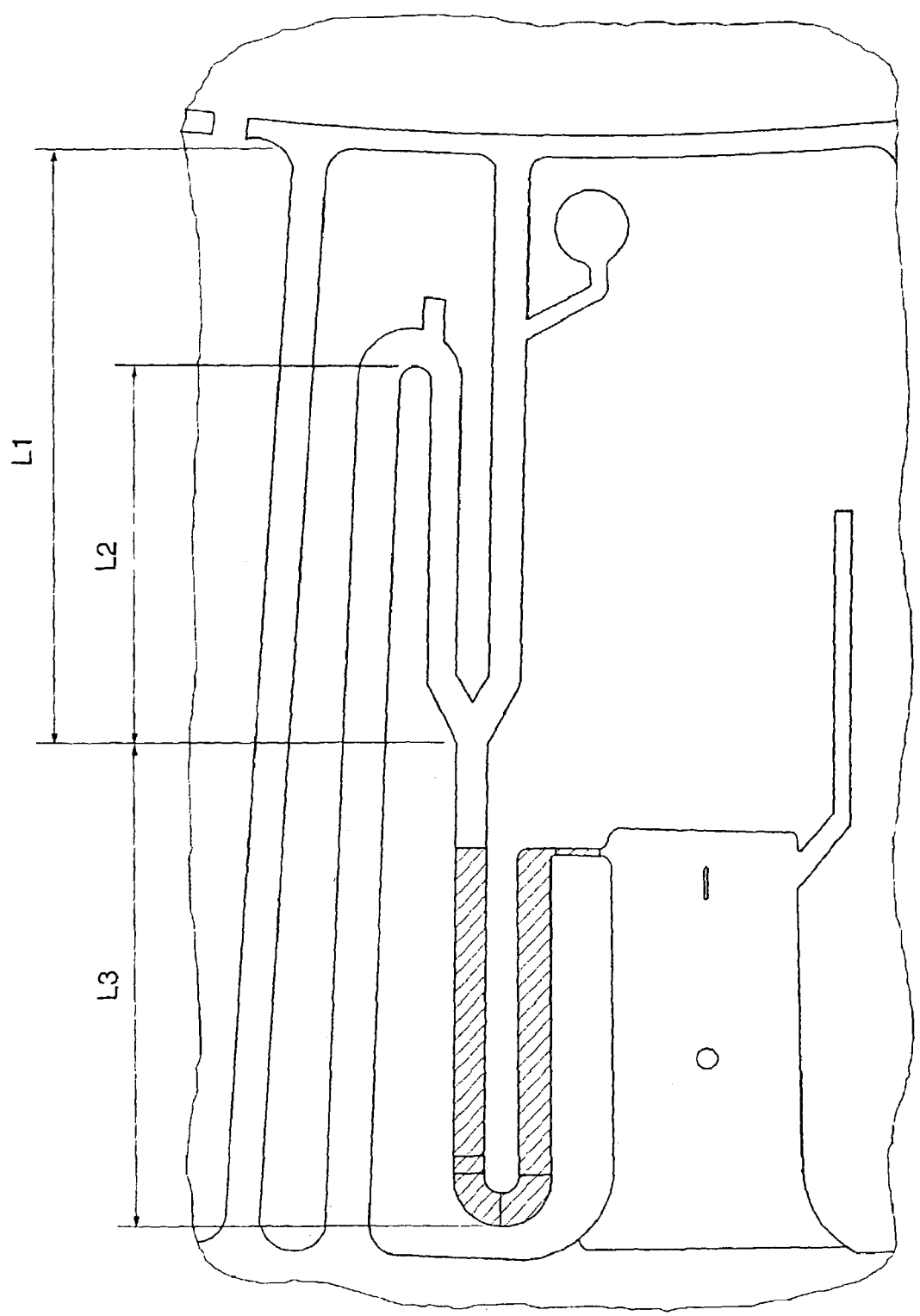

All of the first fluid X in the chamber (10) can be displaced by the second fluid Y by spinning the disc if the volume of the second fluid in the volume-defining structure (7) and any air between the first and second fluids is equal to or greater than the volume of the first fluid X in the chamber (10). This can be achieved by ensuring that the volume of the volume-defining structure (7) is greater than the volume of the chamber (10). This can be achieved by making the arms (7a) and (7b) of the volume-defining structure longer than the arms of the chamber (10), and/or by making the cross-sectional area of the arms of the volume-defining structure (7) greater than that of the arms of the chamber (10). FIG. 4a) shows an intermediate situation where the disc is being spun and centrifugal force causes fluid Y to flow from the volume-defining structure (7) into chamber (10), thereby displacing first fluid X which flows to waste via restricted channel (11). Any excess second fluid Y flows out of the chamber (10) through the restricted channel (11) into waste chamber (4). FIG. 4b) shows that the second fluid Y has replaced the first fluid X. This process can be repeated using different fluids as often as is desired.

In the event that the fluids contain particles and it is desired to hold them in the chamber it is possible to provide the chamber (10) with a particle filter (21) with suitable sized orifices. In the event that it is necessary to only temporarily hold the particles in the chamber (10) then the sections I, II, III, IV of the chamber (10) which have different depths can be used to temporarily trap the particles. This is done by increasing the speed of rotation of the disc so that the particles collect at the boundary wall between two sections while the fluid flows over the wall.

Figure 5:
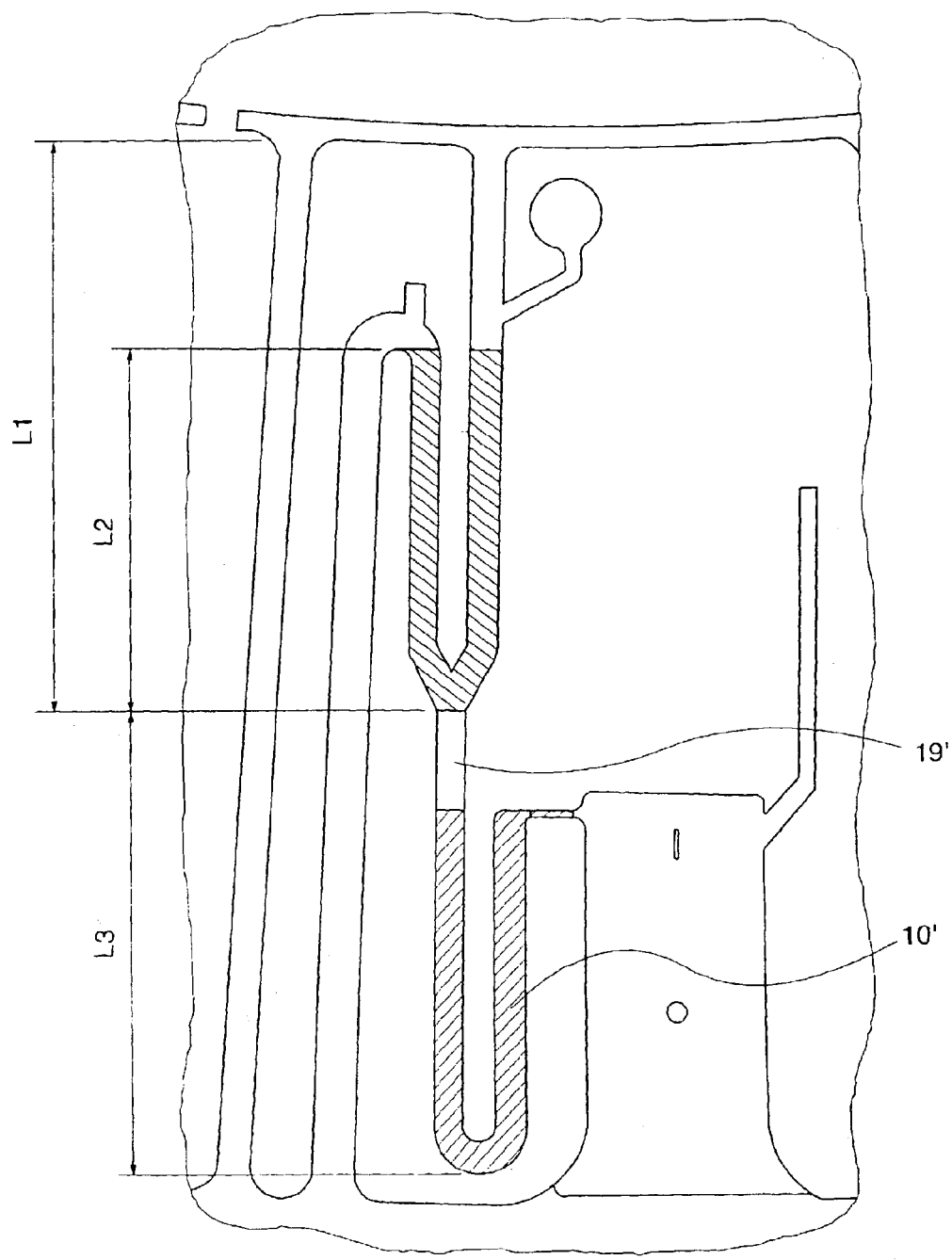
FIG. 5 shows a second embodiment of a microchannel structure in accordance with the present invention.

In another aspect of the invention, particles can be selectively held in, or flushed out of a chamber (10'), which does not have a particle trap or sections having different depths as shown in FIG. 5. This can be achieved as follows:

Particles that have been sedimented, or otherwise collected, in the bottom of the chamber (10') can be drawn out of the chamber (10') by the meniscus of a fluid which flows out of the chamber (10'). In other words, if there is an air cushion (19') between the volume-defining structure and the chamber (10') and this is driven through the chamber, then as the meniscus between the fluid in the chamber and the air cushion passes the particles they are entrained by the meniscus and flow out of the chamber. This can be achieved by choosing a suitably low rate of acceleration of the disc (known as "ramp speed"). If however it is desired to retain the particles in the chamber then it is necessary to ensure that the air cushion is not driven through the chamber (10') by the fluid in the volume-defining structure when the disc is spun. If a suitably high rate of acceleration of the disc is chosen, it is possible to cause the fluid in the volume-defining structure to flow down the sides of the channel, through the air cushion (19'), without displacing the air cushion (19'). Typically a ramp speed of up to 3500 rpm/s$^2$ transports the particles further in the channel system. With a ramp speed greater than 3500 rpm/s$^2$ the fluid/air interface (meniscus) does not enter the U-chamber and the air bubble stays still or moves in the opposite direction to the centrifugal force. The exact ramping speeds to achieve the desired effect are naturally dependent on the type of fluid used and are most suitably determined by experimentation.

Figure 6:
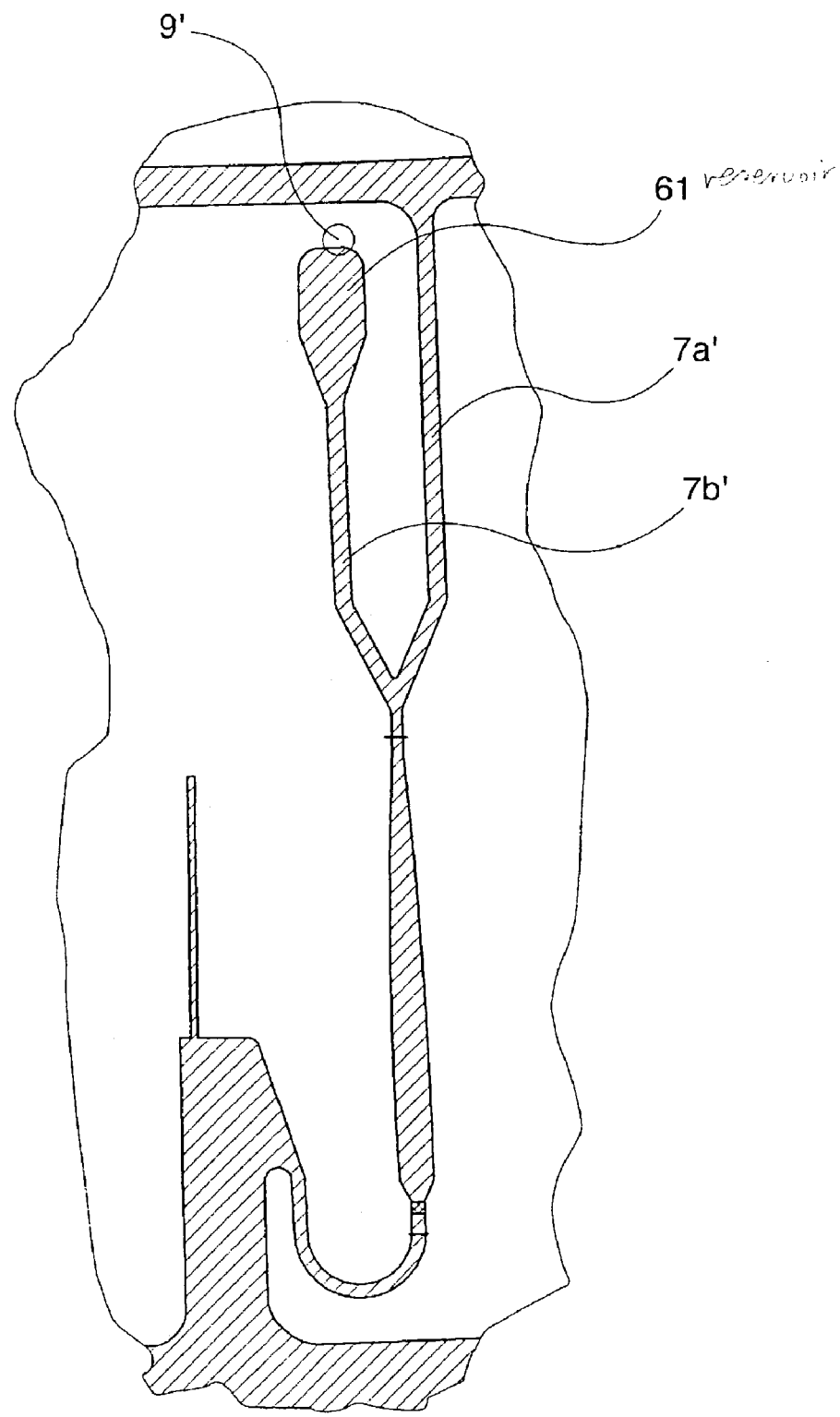
FIG. 6 shows a third embodiment of a microchannel structure in accordance with the present invention.

In another embodiment of the invention, as shown in FIG. 6, the arm (7b') of the volume-defining structure (7') is not connected to a waste channel (8), but is instead enlarged at its end nearest the centre of the disk in order to form a reservoir (61) for fluid to prevent fluid overflowing out of a vent (9'). This vent and/or sample inlet (9') vents this reservoir (61) to atmosphere and can also permit samples to be introduced into the structure. The reservoir (61) preferably has a length which makes the length of the volume defining structure i.e. reservoir (61) and arm (7b') equal to or greater than the length of arm (7a'). If the vent (9') is made so small that the surface tension of the fluid prevents it from flowing out of the vent when the volume-defining structure (7') is being charged by spinning, then the amount of fluid which can enter the volume-defining structure (7') is minimised and no fluid is wasted. Naturally if it is desired to replace all the fluid in the chamber (10) with fluid from the volume defining structure then the volume of the volume defining structure must be greater than the volume of the chamber (10). If the arm (10a) of the chamber is made to widen from its upper end to its lower end then it is possible to push the air barrier (19) out of the chamber when adding a second fluid without the two fluids mixing.

Figure 7:
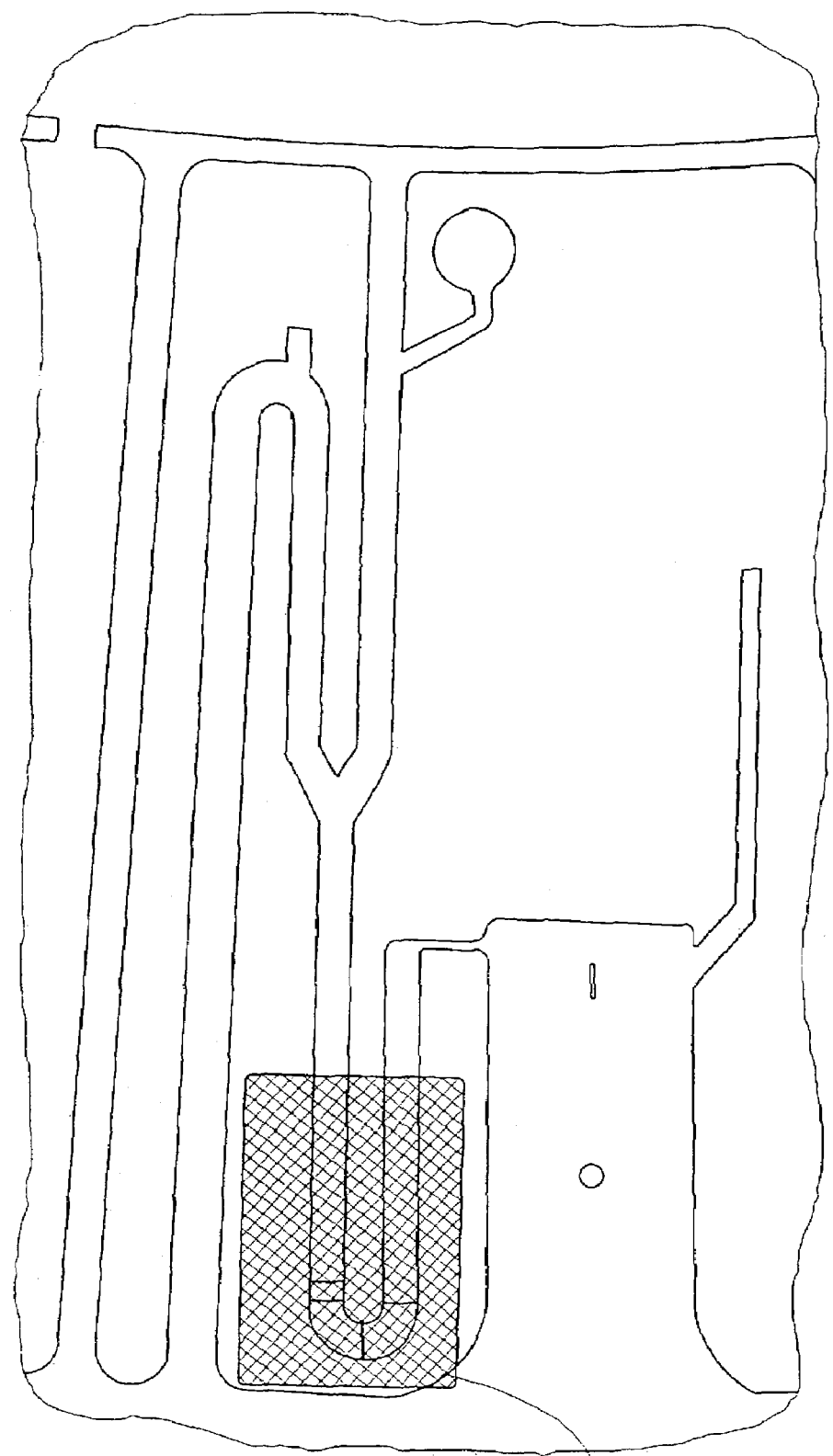
FIG. 7 shows a fourth embodiment of a microchannel structure in accordance with the present invention.

All the chambers of the present invention can be provided with heating means in the form of a coating as shown crosshatched in FIG. 7. This coating (71), which can be painted or printed or applied in some other way to one or both sides of the disk in the vicinity of the chamber, can absorb energy from electromagnetic radiation which is directed onto it and thereby heat up the chamber. The incident radiation can be infra red light, laser light, visible light, ultraviolet light, microwaves or any other suitable type of radiation. The heating up of the chamber can be used to initiate or accelerate reactions in the chamber. If the disk is stationary while the chamber is being heated then if the fluid boils it will produce bubbles of vapour which will travel up the arms of the chamber and may even pass out into the waste channel (8) and waste chamber (4). This is not always desirable as it is often preferred that substantially all the fluid should remain in the chamber after the heating has been finished. This can be achieved in the present invention by spinning the disk at the same time that radiation is incident on the coating (71). The radiation sources (not shown) can be focused onto areas that the coating passes through as the disc spins. Furthermore the coating can be dimensioned such that heat is only applied to only the smallest amount of the base consistent with adequate heating of the reagents. In this way the arms of the U are keep cool and provide condensation surfaces for the fluid vapour to condense on. The centrifugal force exerted on the condensed vapour causes it to flow back into the base of the chamber.

Figure 8:
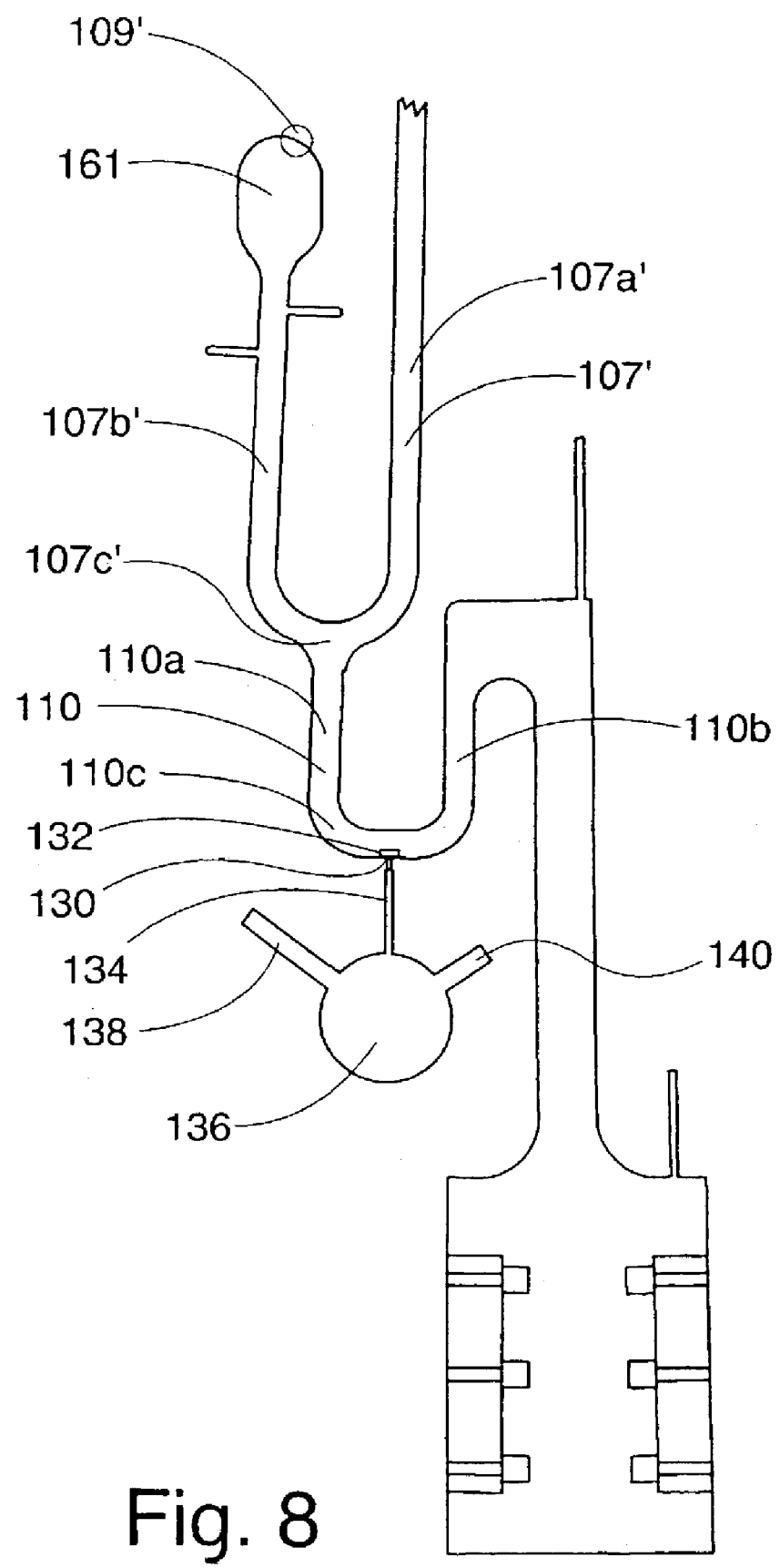
FIG. 8 shows a fifth embodiment of a microchannel structure in accordance with the present invention.

Note that while the embodiments of the invention described above have a chamber leading to a waste chamber, it is of course conceivable that the chamber outlet leads to one or more further chamber(s). Each further chamber may have a plurality of inlets and a plurality of outlets so that samples and reagents may be combined in a chamber. The subsequent results of any process, which has taken place in a chamber, can be dispensed to one or more additional chambers for further processing or sent to the waste channel. An example of this is shown in FIG. 8. FIG. 8 shows a microstructure, of a design similar to that shown in FIG. 6, in which the base (110c) of U-shaped chamber (110) is connected by a base outlet channel (134) to a second chamber (136), which second chamber (136) is positioned further away from the centre of the disk than second chamber (110). Second chamber (136) is vented to atmosphere by a vent (138) that opens out on the top surface of the disc. Second chamber (136) is also provided with an inlet/outlet connection (140) that also opens out on the top surface of the disk. Inlet/outlet (140) can be used to supply substances to second chamber (136) e.g. by injecting them into connection (140) and/or to extract substances from second chamber (136) e.g. by sucking them out via connection (140). Fluid is prevented from flowing by capillary action from chamber (110) into base outlet channel (134) by a hydrophobic break (132) positioned at or near the junction (130) between the base (110c) of chamber (110) and base outlet channel (134). Hydrophobic break (132) is dimensioned so that when the disc is spun at a certain number of revolutions per second then any fluid in chamber (110) leaves the chamber via chamber outlet arm (110b), and when the disc is spun at a higher number of revolutions per minutes then the centrifugal force acting on the fluid is sufficient to overcome the hydrophobic effect of hydrophobic break (132) and the fluid flows into second chamber (136). In this embodiment of the present invention, the outlet arm (110*b*) of chamber (110) is almost as long as inlet arm (110*a*). Thus when chamber (110) is filled with a fluid the level of fluid in inlet arm (110*b*) will be very close to the base (107*c*') of the volume-defining structure (107'). This means that when a second fluid is supplied to the volume-defining structure (107'), e.g. via inlet (109') in the reservoir (161), it will come into direct contact with the first fluid in the chamber (110) and no air bubble will form between the two fluids. This arrangement can be used to facilitate mixing of two fluids.

The above mentioned examples of conceivable embodiments are intended to illustrate the present invention and are not intended to limit the scope of protection claimed by the following claims.

The invention claimed is:

1. A microstructure for fluids provided in a rotatable disk comprising:
   a first U-shaped volume-defining structure comprising:
      a first arm connected at or near its upper end to an entrance port wherein the lower end of said first arm is further from the center of said disk than said entrance port;
      a second arm connected at or near the upper end to a first waste channel, a sample inlet or a vent via a reservoir for fluid; and
      a base positioned further from said center of said disk than said first and second arms, wherein said base connects the lower ends of said first and second arms and wherein at least the first arm of the first U-shaped structure is adapted to drive fluid flow by capillary action from the entrance port into the first U-Shaped structure;
   a second U-shaped chamber comprising:
      an inlet arm, wherein said inlet arm is connected to said base of the U-shaped volume defining structure, at or near to the upper end of said inlet arm,
      an outlet arm, wherein said outlet arm is connected at or near its upper end to a second waste channel; and
      a base, wherein said base connects the lower end of said inlet arm to the lower end of said outlet arm, and said base is further from, or the same distance from, the center of said disk than the lower ends of said inlet and outlet arms of said U-shaped chamber; and
   a barrier means for preventing capillary action between the first U-shaped volume defining structure and the second U-shaped chamber, wherein the barrier means comprises a hydrophobic break.

2. The microstructure of claim 1, wherein said first waste channel is provided with a vent.

3. The microstructure of claim 1, wherein the resistance to fluid flow through said second waste channel is greater than the resistance to fluid flow through said first waste channel.

4. The microstructure of claim 1, wherein said U-shaped chamber is at least partly covered by a coating that can absorb energy from electromagnetic radiation which is directed onto it and thereby heat up said chamber.

5. The microstructure of claim 1, wherein said U-shaped chamber has sections I, II, III, IV which have different depths and which can be used to trap and release sedimenting material or other particles.

6. The microstructure of claim 1, wherein said U-shaped chamber is connected by its base to a second chamber positioned further from said center of said disk than said chamber by means of a channel, wherein there is a hydrophobic break positioned at or near the junction between the chamber and the channel.

7. A method for dispensing a predetermined volumes volume of fluid to a chamber, which comprises utilizing the microstructure of claim 1, comprising the steps of:
   (a) providing the microstructure of claim 1 wherein the chamber is the U-shaped chamber with said predetermined volume provided in the U-shaped volume-defining structure, and
   (b) transporting the volume into the chamber by rotating the microstructure.

8. A method for replacing an original fluid in a chamber in a rotatable disk comprising the steps of:
   providing the microstructure of claim 1 having said original fluid in chamber;
   filling said volume-defining structure with a replacement fluid; and
   rotating said disk at a sufficiently high speed such that said replacement fluid moves under centrifugal force into said chamber while at the same time the original fluid in the chamber is forced out of the chamber by the incoming replacement fluid.

9. The microstructure of claim 1, wherein the second arm is connected to the vent or the sample inlet.

10. The microstructure of claim 1, wherein the second arm is connected to said vent via a reservoir for fluid.

11. The microstructure of claim 1, wherein the second arm is connected to said vent and a sample inlet.

12. The microchannel structure of claim 1, wherein the microstructure supports capillary transport of fluid within the structure.

13. The microchannel structure of claim 1, wherein said first waste channel has an outlet end that is further from the center of the disc than the intersection of the inlet arm of the U-shaped chamber to the base of the U-shaped volume-defining structure.

14. The microchannel structure of claim 1, wherein said first waste channel has
   a) an outlet end that is further from the center of the disc than the intersection of the inlet arm of the U-shaped chamber to the base of the U-shaped volume-defining structure, and
   b) a localized region of hydrophobicity that is further from the center of the disc than the intersection of the inlet arm of the U-shaped chamber to the base of the U-shaped volume-defining structure.

15. The microchannel structure of claim 1, wherein the barrier means comprises an air cushion.

16. The microchannel structure of claim 1, wherein the barrier means comprises the arms of the U-shaped volume-defining structure are longer than the arms of the U-shaped chamber.

17. The microchannel structure of claim 1, wherein the barrier means comprises the cross-sectional area of the arms of the U-shaped volume-defining structure are greater than the cross-sectional area of the arms of the U-shaped chamber.

18. A microchannel structure for fluids provided in a rotatable disk comprising:
   a first U-shaped volume-defining structure comprising:
      a first arm connected at or near its upper end to an entrance port wherein the lower end of said first arm is further from the center of said disk than said entrance port;

a second arm connected at or near the upper end to a first waste channel, a sample inlet or a vent via a reservoir for fluid; and a base positioned further from said center of said disk than said first and second arms, wherein said base connects the lower ends of said first and second arms and wherein at least the first arm of the first U-shaped structure is adapted to drive fluid flow by capillary action from the entrance port into the first U-Shaped structure;

a second U-shaped chamber comprising:

an inlet arm, wherein said inlet arm is connected to said base of the U-shaped volume defining structure, at or near to the upper end of said inlet arm, an outlet arm, wherein said outlet arm is connected at or near its upper end to a second waste channel; and a base, wherein said base connects the lower end of said inlet arm to the lower end of said outlet arm, and said base is further from, or the same distance from, the center of said disk than the lower ends of said inlet and outlet arms of said U-shaped chamber, and a localized region of hydrophobicity at the intersection of the inlet arm of the U-shaped chamber to the base of the U-shaped volume-defining structure.

19. A microchannel structure for fluids provided in a rotable disk comprising:

a first U-shaped volume-defining structure comprising:

a first arm connected at or near its upper end to an entrance port wherein the lower end of said first arm is further from the center of said disk than said entrance port;

a second arm connected at or near the upper end to a first waste channel, a sample inlet or a vent via a reservoir for fluid; and a base positioned further from said center of said disk than said first and second arms, wherein said base connects the lower ends of said first and second arms and wherein at least the first arm of the first U-shaped structure is adapted to drive fluid flow by capillary action from the entrance port into the first U-Shaped structure;

wherein said first waste channel has a) an outlet end that is further from the center of the disc than the intersection of the inlet arm of the U-shaped chamber to the base of the U-shaped volume-defining structure, and b) a localized region of hydrophobicity that is further from the center of the disc than the intersection of the inlet arm of the U-shaped chamber to the base of the U-shaped volume-defining structure; and a second U-shaped chamber comprising:

an inlet arm, wherein said inlet arm is connected to said base of the U-shaped volume defining structure, at or near to the upper end of said inlet arm, an outlet arm, wherein said outlet arm is connected at or near its upper end to a second waste channel; and a base, wherein said base connects the lower end of said inlet arm to the lower end of said outlet arm, and said base is further from, or the same distance from, the center of said disk than the lower ends of said inlet and outlet arms of said U-shaped chamber.

20. A microstructure for fluids provided in a rotable disk comprising:

a first U-shaped volume-defining structure comprising:

a first arm connected at or near its upper end to an entrance port wherein the lower end of said first arm is further from the center of said disk than said entrance port;

a second arm connected at or near the upper end to a first waste channel, a sample inlet or a vent via a reservoir for fluid; and a base positioned further from said center of said disk than said first and second arms, wherein said base connects the lower ends of said first and second arms and wherein at least the first arm of the first U-shaped structure is adapted to drive fluid flow by capillary action from the entrance port into the first U-Shaped structure; and a second U-shaped chamber comprising:

an inlet arm, wherein said inlet arm is connected to said base of the U-shaped volume defining structure, at or near to the upper end of said inlet arm, an outlet arm, wherein said outlet arm is connected at or near its upper end to a second waste channel; and a base, wherein said base connects the lower end of said inlet arm to the lower end of said outlet arm, and said base is further from, or the same distance from, the center of said disk than the lower ends of said inlet and outlet arms of said U-shaped chamber, and said U-shaped chamber is connected by its base to a second chamber positioned further from said center of said disk than said chamber by means of a channel, wherein there is a hydrophobic break positioned at or near the junction between the chamber and the channel.

* * * * *